US005578296A

United States Patent [19]

Kashino et al.

[11] Patent Number: 5,578,296
[45] Date of Patent: Nov. 26, 1996

[54] DECOMPOSITION OF MELANIN USING A CULTURE OF BASIDIOMYCETES FUNGUS

[75] Inventors: Yoshinori Kashino; Tomoaki Nishida; Yoshimasa Takahara, all of Tsukuba, Japan

[73] Assignee: Kabushiki Kaisha Kobe Seiko Sho, Kobe, Japan

[21] Appl. No.: 14,876

[22] Filed: Feb. 8, 1993

[51] Int. Cl.$^6$ .............................. A61K 7/135; A61K 7/48; A61K 35/70
[52] U.S. Cl. ........................ 424/62; 424/DIG. 3; 514/783; 514/844; 435/911; 8/101
[58] Field of Search ........................... 424/62, 400, 93 Q, 424/195.1, 93.5; 514/783, 844; 435/254, 265, 268, 911; 8/101

[56] References Cited

U.S. PATENT DOCUMENTS

| | | | |
|---|---|---|---|
| 4,503,041 | 3/1985 | Kashwayama | 435/171 |
| 4,696,813 | 9/1987 | Higa | 514/844 |
| 4,847,074 | 7/1989 | Hatae et al. | 514/844 |

FOREIGN PATENT DOCUMENTS

| | | |
|---|---|---|
| 48-44442 | 6/1973 | Japan . |
| 53-142515 | 12/1978 | Japan . |
| 0225423 | 9/1986 | Japan . |
| 0278414 | 7/1990 | Japan . |

OTHER PUBLICATIONS

Makato Seiji, et al., "Cell", 4, (9), pp. 16–25 (1972).
Toshio Hamada, "Japanese Journal of Clinical Dermatology" 44, (6), pp. 629–633 (1990).
Junichi Miyazaki, "External Preparation for Skin; Preparative Method and Application", pp. 273–275, 353–355, Nanzando Press.
Ryoichi Fukushiro, et al., "Diagnostic and Therapy in Dermatology", vol. 4, pp. 38 & 39, Kodansha Press.
"Recent Science of Cosmetics", Cosmetic Science Research Group eds, Yakuji Nippo Corporation, (1986).
Makato Seiji, "Protein, Nucleic Acid and Enzyme", vol. 15, No. 5, pp. 550–559 (1970).

Primary Examiner—Edward J. Webman
Attorney, Agent, or Firm—Oblon, Spivak, McClelland, Maier & Neustadt, P.C.

[57] ABSTRACT

Melanin is decomposed and decolored, by using a species of *Basidiomycetes* having melanin decomposing potency, which can be applied to whitening cosmetics for treating chloasma and freckle, and additionally, to the decoloring of melanin containing (foodstuff) industrial products.

14 Claims, 2 Drawing Sheets

DECOMPOSITION OF MELANIN USING A CULTURE OF BASIDIOMYCETES FUNGUS

BACKGROUND OF THE INVENTION

1. Field of the Invention

The present invention relates to a melanin decomposing method comprising using a microorganism, especially a species of *Basidiomycetes* having melanin decomposing potency. The present invention also relates to a melanin decomposing substance and a whitening cosmetic.

2. Description of the Related Art

Melanin is biologically synthesized in central nerve and retina in addition to skin in animals and is further present in widespread manner in nature from plants to microorganisms. Melanin is synthesized as follows; firstly, the precursor tyrosine is transformed into a second precursor dopa and then a subsequent precursor dopa-quinone via the action of tyrosinase, and is further oxidized into the precursor indole-5,6-dihydroquinone, which is then polymerized into melanin (Protein, Nucleic Acid and Enzyme, Vol.15, pp.550 (1970)). As utilized herein the term "precursor" includes tyrosine, dopa, dopa-quinone and indole-5,6-dihydroquinone, all of which are known precursors in the biological synthesis of melanin.

Melanin is synthesized in melanocytes, cells present in the epidermal basal layer, the reaction thereof is stimulated by ultraviolet ray (often referred to as UV ray hereinafter) (Ryo-ichi Fukushiro et al., "Diagnostics and Therapy in Dermatology; Vol.4", Kodansha Press, pp.38). In melanocyte, melanin is synthesized and matured in the granules referred to as melanosome. Subsequently, melanin migrates to epidermal cells and is then dispersed therein, where melanin is decolored following dermal metabolism and then scaled off in the form of dirt at the time of the renewal (Cell, 4, (9), P.16(1972)). As has been described above, melanin is a factor of clinical importance, because it is responsible for a significant function for protecting physical bodies against adverse effects of UV ray. However, a higher level of melanin causes darker skin. Furthermore, the heterogeneous distribution thereof causes chloasma and freckling, involving serious problems in terms of beauty.

Hitherto known countermeasures against chloasma and freckling are broadly classified in two preventive methods and one therapeutic treatment.

The following methods have been known as such preventive methods;

1.) a method for shielding skin from UV ray which triggers melanin biosynthesis via sun screening agents and the like ("Recent Science of Cosmetics", Cosmetic Science Research Group eds., Yakuji Nippo Corporation (1986)); and 2.) a method comprising using melanin biosynthesis-inhibiting pharmaceutical agents, for example, melanin synthesis-inhibiting agents such as glutathione, vitamin C, cysteine, arbutin and sodium thiosulfate (Japanese Patent Laid-open Nos. Sho. 53-142515 and Sho. 48-44442).

Presently, however, no safe method without side effects has been developed yet so as to therapeutically treat and eliminate chloasma and freckles once formed (Ryo-ichi Fukushiro et al., "Diagnostics and Therapy in Dermatology; Vol.4", Kodansha Press, pp.38; Jun-ichi Miyazaki, "External Preparation for Skin; Preparative method and Application", Nanzando Press, pp.273–275, 353–355). As a bleaching agent for skin, hydroquinone, 4-isopropylcatechol, and hydroquinone monobenzyl ether and the like have been made use of in the past, but because of their strong whitening action based on the degeneration and death of pigment cells, their continuous external application possibly may cause eternal leucoderma, unavoidably involving side effects such as dyschromatosis and rash. Therefore, the development of a safe pharmaceutical agent for treating chloasma and freckle has been expected earnestly in the industry (Japanese Journal of Clinical Dermatology, 44, (6), pp.629 (1990)).

It is known to treat freckles by shortening the period in which melanin is scaled off following epidermal metabolism. This is accomplished by using agents to soften and peel off the keratin. Typical agents are resorcin and salicylic acid. One such method for therapeutically treating chloasma and freckles is described by Jun-ichi Miyazaki, "*External Preparation for Skin; Preparative Method and Application*", Nanzando Press, pp. 273–275, 353–355. However, these methods cannot be regarded as a method for essentially treating chloasma and freckle; and the methods require a long period of time lasting several months for the treatment, which cannot be said as a practical therapy.

SUMMARY OF THE INVENTION

The present invention has been achieved in such circumstances. It is an object of the present invention to develop a novel system for treating chloasma and freckle once formed in safe manner which system has never been developed conventionally.

It is another object of the present invention to develop a novel system capable of in vivo and in vitro decomposition of melanin because the primary etiology of chloasma and freckle is melanin, which is also contained in xenobiotic substances other than in skin such as a variety of colored products, there being a significant demand for methods of decoloring xenobiotic substances from industry.

For the purpose of achieving the above objects, the present inventors have made investigations from various respects, and drawing attention toward biological treatment from the respect of safety, the inventors have carried out intensive screenings of microorganisms therefor, but without any success. The inventors have innovatively focused their attention to wood rotting fungi with no relation to melanin decomposition.

Among wood-rotting fungi, success has been made of the screening of a microorganism having melanin decomposing potency, thus leading to the achievement of the present invention. The novel, fundamental technical conception of the present invention resides in decomposing melanin using the cultured product of a species of *Basidiomycetes* having melanin decomposing potency or the processed product thereof.

DESCRIPTION OF THE PREFERRED EMBODIMENTS

Figure 1:
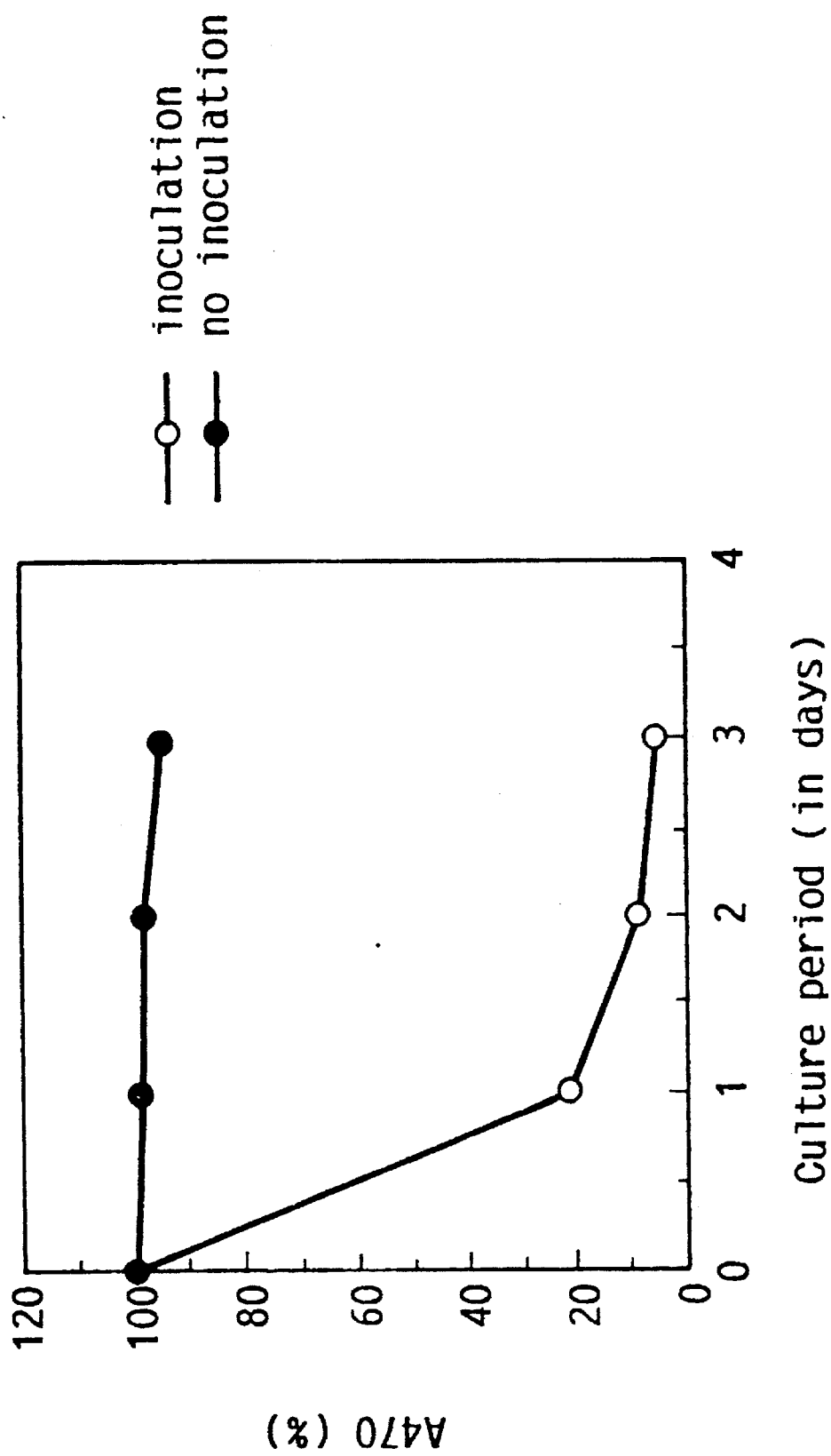
FIG. 1 is a graph depicting the melanin decomposing potency of a species of *Basidiomycetes* having melanin decomposing potency under the condition of liquid culture (the decoloring of melanin is apparently indicated from the decrease in the absorbance at 470 nm over time in the case of the fungal inoculation compared with the case without such fungal inoculation).

Any of wood-rotting fungi having melanin decomposing potency may be usable as the microorganism of the present invention. It does not matter whether the fungus is white wood-rotting fungus or brown wood-rotting fungus. It is advantageous to use, for example, strain NK-1148 (FERM BP-1859) and microorganisms of genus Porodisculus.

The strain NK-1148, a microorganism the present inventors have isolated, is an excellent melanin decomposing fungus. The mycological, nature thereof is described in Japanese Patent Publication No. Hei 3-32996 in detail, and the principal nature is as follows:

A. Growth State in Culture Medium

The growth state is as shown in the following Table 1.

TABLE 1

| Type of culture medium | Growth state |
| --- | --- |
| Malt extract agar medium | +++ |
| Potato-glucose agar medium | +++ |
| Zapeck agar medium | + |
| Sabouraud agar medium | ++ |
| Defined Mucor agar medium | ++ |
| YpSs agar medium | +++ |
| Glucose-dry yeast agar medium | +++ |

Note 1. Medium pH: 5.0 (prior to autoclave sterilization)
Note 2. Culture condition: 28° C. × 7 days
Note 3. Growth state
slight: +
moderate: ++
vigorous: +++

B. Physiological and Biological Properties

1. Growth pH range (Culture in potato-glucose agar medium at 28° C. for 4 days)

The fungus grows around pH 3 to 9, but does not grow at pH 2 or 10. The optimum pH is around 4 to 6.

2. Growth temperature range (Culture in potato-glucose agar medium, pH 5 for 4 days)

The fungus grows at about 10° to 45° C., but does not grow at 50° C. The optimum temperature is around 28° to 37° C.

3. Phenol-oxidase reaction (Culture at 28° C. for 4 days)
Slight or negative reaction is observed.

4. Characteristic properties of mycelial tuft (Culture in potato-glucose agar medium, pH 5 at 28° C. for 4 days)
White in a felt-like form.

Detailed examination was done about the fungal properties such as these physiological and biological properties and the growth state in the individual media. Consequently, it was found that the fungus could not be identified as a known fungus. Therefore, the fungal strain was identified as novel one and designated as strain NK-1148, which was subsequently deposited in The Patent Microorganism Depository, Fermentation Research Institute, Agency of Industrial Science and Technology, The Ministry of International Trade and Industry, at 1–3, Higashi 1-chome, Tsukuba-shi, Ibaraki-ken, 305, Japan (FERM BP-1859; the original deposition date: May 23, 1987).

The fungi of genus Porodisculus include illustratively a strain NK-729W of *Porodisculus pendulus* (FERM BP-1860), which was successfully isolated firstly by the present inventors. The subject fungal strain is excellent in terms of the high melanin decomposition potency thereof. Japanese Patent Publication No. Hei 3-32997 describes the strain's properties in details, and the major ones are as follows.

A. Growth State in Culture Medium

The growth state is as shown in the following Table 2.

TABLE 2

| Type of culture medium | Growth state |
| --- | --- |
| Malt extract agar medium | +++ |
| Potato-glucose agar medium | +++ |
| Zapeck agar medium | + |
| Sabouraud agar medium | ++ |
| Defined Mucor agar medium | ++ |
| YpSs agar medium | +++ |
| Glucose-dry yeast agar medium | +++ |

Note 1. Medium pH: 5.0 (prior to autoclave sterilization)
Note 2. Culture condition: 28° C. × 7 days
Note 3. Growth state
slight: +
moderate: ++
vigorous: +++

B. Physiological and Biological Properties

1. Growth pH range (Culture in potato-glucose agar medium at 28° C. for 4 days)

The fungus grows around pH 3 to 7, but does not grow at pH 2 or 8. The optimum pH is around 4 to 5.

2. Growth temperature range (Culture in potato-glucose agar medium, pH 5 for 4 days)

The fungus grows at about 10° to 32° C., but does not grow at 37° C. The optimum temperature is around 20° to 30° C.

3. Phenol-oxidase reaction (Culture at 28° C. for 4 days)
Positive reaction is observed.

4. Characteristic properties of mycelial tuft (Culture in potato-glucose agar medium, pH 5 at 28° C. for 4 days)
White in a hairy form.

5. Morphology of fruit body
Size: 2–5 mm in diameter
Shape: form of inverted bowl (shape of the lower nasal part)
Circumference and surface: the circumference is rolled inside; the surface is yellowish brown, with brown hair all over.
Tubular hole surface: lightly grayish white, having recesses in the form of inverted bowl, the tube is small.
Flesh: soft skin quality; almost white.

6. Spore morphology
Spores are of a form of sausage and of about 3 to 4 ×1 μm; colorless and smooth.

Based on these mycological properties, it was appropriately determined that the subject fungus belongs to genus Porodisculus and specifically belongs to *Porodisculus pendulus*. Thus, the fungus was designated as *Porodisculus pendulus* NK-729W and deposited in The Patent Microorganism Depository, Fermentation Research Institute, Agency of Industrial Science and Technology, The Ministry of International Trade and Industry, at 1–3, Higashi 1-chome, Tsukuba-shi, Ibaraki-ken, 305, Japan ( FERM BP-1860; the original deposition date: May 23, 1987).

In accordance with the present invention, the cultured product and/or the processed product of a fungus body of *Basidiomycetes* having melanin decomposing potency in addition to the fungus body may also be usable. By the term "cultured product" is meant broadly a mixture of the fungus body obtained by culturing a fungus and the culture medium thereof. In accordance with the present invention, there may be used the fungus body in wet cake or the like isolated from the fungal cultured product, the residue thereof and the culture medium obtained after removing all of solid matters. By the term "processed product" is meant all obtained after condensation, drying or diluting those described above.

To decompose melanin in accordance with the present invention, the fungus body, cultured product and/or processed product of a species of *Basidiomycetes* having melanin decomposing potency should be brought into contact with the melanin. If desired, the contact may be conducted under conditions of incubation at around 10°–45° C. for the time necessary to decompose melanin. It is desirable that the contact be conducted under conditions of nitrogen limitation. Preferably, the contact is conducted in the absence of a nitrogen source or under conditions wherein the amounts of nitrogen present are as low as possible. Furthermore, the concurrent use of glucose then is more advantageous.

The melanin decomposing substance of the present invention may be formulated into oral preparations in solid, semi-solid or liquid form or parenteral preparations such as external preparations and bathing preparations, by employing the fungus body, cultured product and/or processed product of a species of *Basidiomycetes* having melanin decomposing potency as the effective ingredient, and adding thereto general inorganic or organic excipients. For industrial use, only the effective ingredient may be employed.

The formulations for oral administration illustratively include tablets, pills, granules, soft and hard capsules, dispersions, fine granules, powders, emulsions, suspensions, syrups, elixirs and the like. The formulations for parenteral administration include, for example, injections, ointments, lotions, tonics, sprays, suspensions, oils, emulsions, suppositories and the like. For the formulation of the effective ingredient of the present invention, routine methods should be followed, employing appropriately surfactants, excipients, coloring agents, flavorings, preservatives, stabilizers, buffers, suspending agents, isotonic agents and other routinely employed substances.

The melanin decomposing substance according to the present invention should be dosed appropriately, depending on the extent of chloasma and freckles, the administration form, the age and the like. Generally, the dosage is within a range of 0.1 to 100 mg/kg per day as the amount of the effective ingredient per adult for oral and enteral administrations. For external preparations for skin, an appropriate amount thereof should be applied to lesions several times. For industrial applications, the substance should be contacted to a subject for melanin elimination, with no such specific limitation as those described above. No specific toxicity was observed in rats administered with the substance at an oral dose of 100 mg/kg·body weight. Thus, the safety of the substance was concluded.

The present invention also relates to a whitening cosmetic containing the fungus body of a species of *Basidiomycetes* having melanin decomposing potency, the cultured product and/or processed product thereof as the effective ingredient. The whitening cosmetic of the present invention is mainly for external applications for skin in the form of skin lotions, creams, milky lotions, packing and bathing agents, hair discoloring agents and the like. To the external bases and auxiliaries generally employed in the individual external preparations is compounded the effective ingredient to 0.001 to 15%, preferably to 0.01 to 10% for preparing external preparations.

A skin lotion may be prepared by dissolving an emollient such as glycerin and propylene glycol, dermal nutrients and the like in distilled water, dissolving an antiseptic, a perfume or the like in alcohol, and then mixing the two together followed by solubilization at room temperature. The effective ingredient of the present invention is added to a water-soluble part thereof to 0.01 to 10%, thereby preparing a skin lotion.

For a general method for preparing a cream comprising preparing an aqueous phase part by adding a hydrophilic component, for example, an emollient such as glycerin, sorbitol and the like in distilled water and preparing an oily phase part by adding an oily component such as an antiseptic, a surfactant or the like to a solid oil such as bee wax, paraffin, microcrystalline wax, serecin, a higher fatty acid, a hardened oil and the like and to a liquid oil such as squalane, liquid paraffin, a variety of ester oils and the like, heating the aqueous phase part thus obtained and gradually adding the oily phase part heated at the same temperature under gradual stirring, thereby producing an emulsified cream, for example, the effective ingredient is added to the aqueous phase part to 0.01 to 10% for preparing a cream.

For a general method for preparing a milky lotion comprising adding an emollient such as glycerin and a pH adjusting agent such as an acid or an alkali to distilled water, mixing them together under heating followed by addition of ethanol to prepare an aqueous phase part, adding an oily component such as an antiseptic and a surfactant to a solid oil component such as bee wax, paraffin and the like, a semi-solid oil component such as vaseline, lanolin and the like, a liquid oil component such as squalane, liquid paraffin, a variety of ester oils and the like, mixing them together under heating to prepare an oily phase part, adding the oily phase part to the aqueous phase part for preliminary emulsification, followed by addition of a protective colloid such as carboxyvinyl polymer, carboxymethyl cellulose and the like, and homogeneously emulsifying the resulting mixture with a homogenizer to prepare a milky lotion, for example, the effective ingredient of the present invention is added to the aqueous phase part to 0.01 to 10% to prepare a milky lotion.

For a general method for preparing a pack comprising adding an emollient such as glycerin, a film-forming agent such as polyvinyl alcohol, bee gum and the like to distilled water for swelling, adding to the mixture a powder such as kaolin, talc, zinc oxide and the like if necessary, further adding ethanol with a perfume and an antiseptic in dissolution, and thereafter kneading the mixture to a paste, for example, the effective ingredient of the present invention is added to 0.01 to 10% for preparing a packing agent. Following general methods, bathing agents and hair decoloring agents are prepared, satisfactorily.

It has been described hereinabove that better results may be obtained in the practice of the present invention if the contact to melanin is carried out under the condition of nitrogen limitation, and far better results may be obtained if employing as a species of *Basidiomycetes* having melanin decomposing potency a microorganism pre-cultured in a broth in the presence of melanin and/or the precursor thereof under the condition of nitrogen limitation. As melanin precursors, appropriate use may be made of a variety of the aforementioned low molecular and high molecular substances generating melanin singly or in combination.

The invention will be understood more readily with reference to the following examples; however these examples are intended to illustrate the invention and are not to be construed to limit the scope of the invention.

EXAMPLE 1

In petri dishes were prepared four types of culture media as follows; potato-dextrose agar medium (containing 2% of glucose), nitrogen-limited defined media (L-N media shown in the following Table 3) with glucose added at 0%, 0.1% and 1%. The ink of a species of cuttlefish (about 50% thereof is composed of melanin) was dispersed therein as a melanin sample.

TABLE 3

| Composition of L-N culture medium | (per liter) |
|---|---|
| Ammonium tartrate | 0.2 g |
| $KH_2PO_4$ | 1 g |
| $NaH_2PO_4$ | 0.2 g |
| $MgSO_4.7H_2O$ | 0.5 g |
| Thiamine hydrochloride | 100 μg |
| 2,2-Dimethyl succinate | 1.46 g |
| $CaCl_2$ | 100 μg |
| $FeSO_4.7H_2O$ | 100 μg |
| $ZnSO_4.7H_2O$ | 10 μg |
| $CuSO_4.5H_2O$ | 20 μg |
| Agar | 1.5% |

Alternatively, a species of *Basidiomycetes*, strain NK-1148 (FERM BP- 1859) having melanin decomposing potency, was inoculated at the circumference of the petri dishes and incubated at 28° C.

Consequently, as shown in Table 4, it was confirmed that the strain NK-1148 can decolor or decompose melanin and that the addition of 1% of glucose to a nitrogen-limited medium (50 μl of the cuttlefish ink solution per 20 ml of the medium shown in Table 3 with 1% of glucose added) shows most excellent decoloring effect, which demonstrates the efficacy of the present invention. The growth of hyphae was most distinctive in the potato-dextrose medium, but no melanin decoloring or decomposition was observed. From what has been described above, it was indicated that the nitrogen limitation is effective for melanin decomposition. When no glucose was added or when glucose was limited to 0.1%, melanin decoloring or decomposition was slight even though the growth of hyphae was observed but it was not vigorous. These indicate that sugar may serve a role for melanin decomposition or decoloring in a certain manner.

As apparently shown in these results, it was demonstrated scientifically that the strain NK-1148 exhibits distinctive melanin decomposing potency.

TABLE 4

The effect of the kind of medium and the amount of glucose added on melanin decomposition of the strain NK-1148

| Medium | radius of decolored area (mm)* |
|---|---|
| L-N medium + 0% glucose | 10 |
| L-N medium + 0.1% glucose | 20 |
| L-N medium + 1% glucose | 63 |
| potato-dextrose agar medium | 0 |

*radius of decolored area after 12 days incubation.

EXAMPLE 2

Strain NK-1148 was inoculated into a liquid medium produced by removing agar from the L-N medium shown in Table 3 and adding 1% of glucose thereto, and cultured therein for one week at 30° C. Adding thereafter 2.5 g of a commercially available synthetic melanin (manufactured by Sigma Chemical Company) for further continuing the culture, the relative absorbance at 470 nm was measured over time so as to confirm the decoloring action. For controls, similar experiments were done with no NK-1148 strain inoculated.

As shown in FIG. 1, consequently, the absorbance was decreased by about 80% one day after the addition of melanin when the strain NK-1148 was inoculated; and three days later, only several % thereof was retained. Thus, it was scientifically demonstrated that melanin is also decolored at a higher degree even in liquid culture.

EXAMPLE 3

Strain Nk-1148 was cultured for 24 hours in the presence of melanin in the same manner as in Example 2. Then whole cultured product thereof was treated via french press, and centrifuged, thus obtained the acellular extract. Adding thereafter the synthetic melanin, the absorbance at 470 nm was measured over time so as to confirm the discoloring action. For controls, similar experiments were done with no acellular extract acted. (All the experiments in this example were done in a liquid medium produced by removing agar from the L-N medium shown in Table 3 and adding 1% of glucose thereto.)

Figure 2:
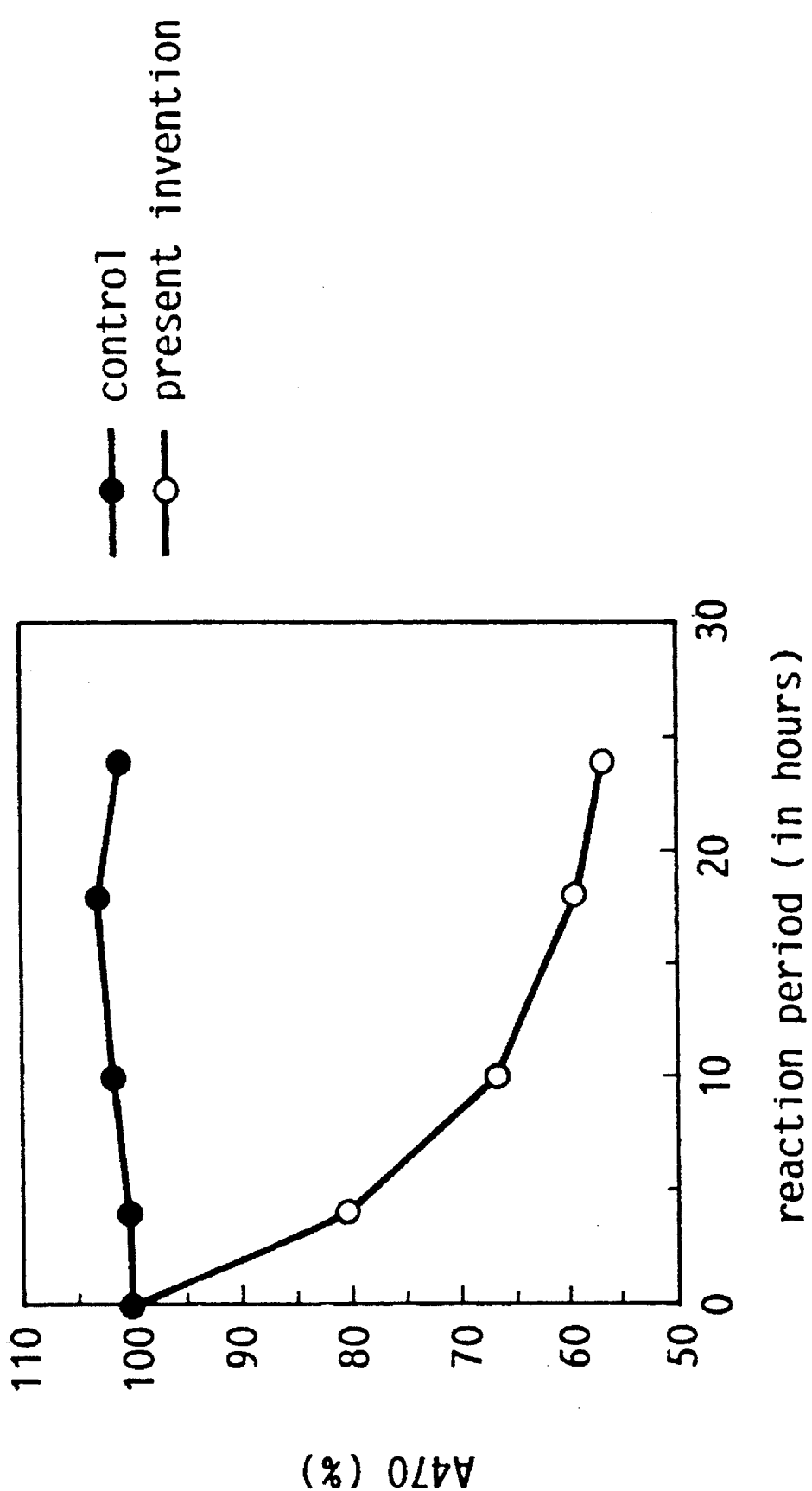
FIG. 2 is a graph depicting the melanin decoloring potency of the cultured product of a species of *Basidiomycetes* having melanin decomposing potency (the decoloring of melanin is apparently indicated from the decrease in the relative absorbance at 470 nm over time in the case of the cell-free extract being acted on melanin.)

As shown in FIG. 2, consequently, the absorbance was decreased by about 50% 24 hours after the addition of melanin. Thus, it was demonstrated that the melanin is also discolored at a higher degree even when using cultured product (an acellular extract) of Strain NK-1148.

EXAMPLE 4

Except for replacing the strain NK-1148 with NK-729W (FERM BP-1860), the same procedures as in Example 1 and 2 were repeatedly followed. Thus, melanin discoloring was confirmed.

EXAMPLE 5

Whitening Skin Cream

Employing a cultured product of the strain NK-1148 cultured in a liquid medium produced by removing agar from the L-N medium shown in Table 3 and adding 1% of glucose and 2 ml of the cuttlefish ink solution, O/W emulsion was prepared at the formulation of Table 5 following the routine method. Thus, a skin cream for treating chloasma and freckle was prepared.

TABLE 5

| Formulation of whitening skin cream | (wt %) |
|---|---|
| Cultured product of strain NK-1148 | 2.0 |
| Stearic acid | 8.0 |
| Cetostearyl alcohol | 5.0 |
| Bee wax | 8.0 |
| Oleic acid monoglyceride | 8.0 |
| Liquid paraffin | 45.0 |
| Sodium cetylalcohol sulfate | 1.5 |
| Methylparaben | 0.2 |
| Distilled water | q.s. to a total volume of 100 |

EXAMPLE 6

Whitening Packing Agent

Employing a cultured product of the strain NK-729W cultured in a liquid medium produced by removing agar from the L-N medium shown in Table 3 and adding 1% of glucose and 2 ml of the cuttlefish ink solution, the group A of the formulation of Table 6 was mixed and dissolved together to prepare a gel according to the routine method, followed by sequential addition of B and C to the A for preparing a packing agent for treating chloasma and freckle.

TABLE 6

| Formulation of whitening packing agent | (%) |
|---|---|
| A. Carboxyvinyl polymer | 1.40 |
| Dipropylene glycol | 10.00 |
| Glycerin | 3.00 |
| Diisopropanol amine | 0.15 |
| B. Triacetin | 30.00 |
| Xanthum gum | 2.00 |
| C. NK-729W cultured product | 2.00 |
| Distilled water | q.s. to 100 |

Only the products for preventing the generation of chloasma and freckle have been developed conventionally as the whitening cosmetics for chloasma and freckle. No success has been achieved yet in developing products for decreasing or eliminating once generated chloasma and freckle, namely, highly safe agents for treating chloasma and freckle.

In contrast, the present invention has successfully achieved firstly the development of an extremely safe agent for treating chloasma and freckle whose development has never been achieved conventionally in spite of all the efforts directed therefor. The present invention brings about distinctive effects in exhibiting such efficacy through not only external application but also oral administration.

The operation of the present invention is based on the distinctive melanin decomposing action, which can be exhibited in vitro as well as in vivo as has been described above and can be applied in industrial field. For example, melanin is also contained in a variety of xenobiotic substances such as colored products and the like. By treating these products with the substance of the present invention, melanin can be decomposed and decolored. Thus, a remarkable advantage can be brought about in that the decoloring of colored industrial products derived from melanin can be performed with efficiency.

Although the invention has been described in its preferred form with a certain degree of particularity, it is understood that the present disclosure of the preferred form has been changed in the details of construction and the combination and arrangement of parts may be resorted to without departing from the spirit and the scope of the invention as threinafter claimed.

What is claimed is:

1. A method for decomposing melanin comprising contacting the melanin with the species of *Basidiomycetes* fungus having melanin decomposing potency, said species being a wood-rotting fungus, and said species being obtained by culturing in a nitrogen limited medium.

2. A method according to claim 1 wherein said nitrogen-limited medium is L-N media.

3. The method as set forth in claim 1 wherein the culture medium contains glucose.

4. A method according to claim 1 wherein said nitrogen-limited medium also contains at least one substance selected from the group consisting of melanin and a precursor thereof.

5. The method of claim 1, wherein said wood-rotting fungus is a lignin-degrading microorganism.

6. A method for decomposing melanin comprising contacting the melanin with a cultured product or processed product thereof of a species of *Basidiomycetes* fungus having melanin decomposing potency, said species being a wood-rotting fungus, said cultured product or processed product being obtained by culturing the fungus in a nitrogen limited medium.

7. A method according to claim 6 wherein said nitrogen-limited medium is L-N media.

8. The method as set forth in claim 6 wherein the culture medium contains glucose.

9. A method as set forth in claim 8 wherein said glucose is present at a concentration of 0.1–1%.

10. A method as in claim 6 wherein said wood-rotting fungus is strain NK-1148 or a microorganism which belongs to the genus Porodisculus.

11. A method as in claim 10 wherein said fungus is the microorganism *Porodisculus pendulus*.

12. A method as in claim 11 wherein said microorganism is NK-729W.

13. A method according to claim 6 wherein said nitrogen-limited medium also contains at least one substance selected from the group consisting of melanin and a precursor thereof.

14. The method of claim 6, wherein said wood-rotting fungus is a lignin-degrading microorganism.

* * * * *